United States Patent [19]

Cobia

[11] Plant 4,607

[45] Nov. 4, 1980

[54] PLANT OF THE BROMELIACEAE FAMILY

[76] Inventor: Barnell L. Cobia, P. O. Box 1307, Winter Garden, Fla. 32707

[21] Appl. No.: 36,542

[22] Filed: May 7, 1979

[51] Int. Cl.[3] ..... A01H 5/12

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety of the Bromeliaceae family is related to the "Zebra plant", the "Pheasant Leaf plant" and the "Stiff Pheasant Leaf plant" and the like these varieties has irregular cross bands. However the new variety is primarily distinguished therefrom by achlorophyllous marginal areas.

2 Drawing Figures

This invention relates to a new and distinct plant variety of the Bromeliaceae family and which has been developed from a vegetative mutation that appeared on a plant specimen of the *Cryptanthus fosterianus* variety. The specimen was under cultivation in a nursery at Winter Garden, Fla. at the time of the discovery and since then, the new variety has been asexually reproduced at the same nursery by the propagation of stem cuttings taken from the specimen.

The *Cryptanthus fosterianus* variety (commonly called the "Stiff Pheasant Leaf plant") is related to the *Cryptanthus zonatus* (commonly called the "Zebra plant") and *Cryptanthus zonatus* 'Zebrinus', (commonly called the "Pheasant Leaf Plant") varieties but is distinguished from the latter two varieties by generally larger specimens that have much thicker and stiffer leaves. All of these varieties are characterized by irregular cross bands, and the new variety is similarly endowed but in contrast to the basic chlorophyllous field that underlies the cross bands in the leaf specimens of the related varieties, the new plant variety is distinguishable therefrom by, among other things, achlorophyllous marginal areas which upon prolonged exposure to sunlight are in color dominated by red, pink, purplish red, purplish pink and/or yellowish pink hues. One objective of the invention has been to develop a new variety of the Bromeliaceae family for the foliage plant market and which is distinguishable from the known varieties related thereto. This objective has been fully realized by the inventor as will be apparent from the plant description which follows herein.

The accompanying drawings serve by color photographic means to illustrate the new variety, one sheet showing a single plant specimen of the new variety while the other sheet provides a photographic closeup of the leaf blades of the new variety.

The following is a detailed description of the new plant variety and is based on observations of well fertilized specimens which were grown in the Central Florida area under approximately 85% shaded nursery conditions and where temperatures are generally maintained in the range from about 15°-30° C. during the winter months and from about 24°-36° C. during the summer months. The description is further based on observations of specimens that were generally 3-6 months in age as determined from the initial propagation of offshoots that were from 2-3 months old.

Except where general terms of ordinary dictionary significance are obviously used, color terminology and color designations reported herein are in accord with the ISCC-NBS Method of Designating Colors are described in the U.S. Department of Commerce, National Bureau of Standards, Circular 553, entitled "ISCC-NBS Method of Designating Colors and Dictionary of Color Terms" with the color designations having been derived from interpretations of Munsell Color Notations obtained by comparing plant specimens with the color specimens in the current "Neighboring Hues Edition" of the Munsell Book of Color, published by Munsell Color Company, Inc., of Baltimore, Md., and to which the reported notations (Munsell Hue, Munsell Value/-Munsell Chromas) are referenced.

Plant Description

Name: *Cryptanthus fosterianus* 'Elaine'.

Origin: A vegetative mutation of a plant of the *Cryptanthus fosterianus* species.

Classification:

A. *Botanic.*—Bromeliaceae or pineapple family.

B. *Commercial.*—Foliage plant.

Form: Terrestrial herb having densely rosulate spreading leaves and bearing rootable offshoots that initiate during or subsequent to anthesis, and with growth terminating with anthesis.

Stems:

A. *General.*—Short, upright and sheathed by overlapping leaves and having a latent bud in the axil areas.

B. *Texture.*—Glabrous and fleshy.

C. *Size.*—1. Length: Usually between 4 and 16 cm. at anthesis. 2. Diameter: Usually between 5 and 25 mm. at anthesis.

Leaves:

A. *General.*—Simple and sessile with stem sheathing leaf bases.

B. *Texture.*—1. Upper epidermal area: Smooth surfaces alternating with transverse, irregular, scurfy bands of minute peltate scales. 2. Lower epidermal area: Lepidote.

C. *Arrangement.*—Rosulate.

D. *Margins.*—Undulating and finely toothed with distally recurving small spines.

E. *Venation.*—Parallel and obscure.

F. *Shape.*—Lorate to linear and trough like with generally undulating margins and an apex area that curves downwardly.

G. *Size.*—1. Length: Usually 10–41 cm. 2. Width: Usually 20–55 mm. at widest area distally of the stem sheathing basal area. 3. Thickness: Usually 1–3 mm. along the axis and thinning laterally thereof toward the margins, and with some evidence of a general taper along the leaf axis toward the tip.

H. *Color.*—1. Upper epidermal surface: (a) General — Achlorophyllous marginal areas which upon prolonged exposure to sunlight are in color dominated by red, pink, purplish red, purplish pink and/or yellowish pink hues and which are separated by an intervening prominent chlorophyllous area that generally extends along and laterally of the leaf axis, the chlorophyllous area occasionally having an axially extending streak that tends to exhibit achlorophyllous characteristics, the upper epidermal surface having overlying irregular transverse scurfy bands. (b) Achlorophyllous marginal areas — commonly dark purplish pink (5 RP 6/8) (7.5 RP 6/8), deep purplish pink (5 RP 6/10) (7.5 RP 6/10), moderate purplish red (7.5 RP 5/10) (near 10 RP 5/10), deep pink (10 RP 6/8) (near 10 RP 6/10) (near 2.5 R 6/8) (near 2.5 R 6/10) (5 R 6/8) (near 5 R 6/10), moderate red (2.5 R 5/10), strong red (5 R 5/12) and/or strong yellowish pink (near 5 R 7/8). (c) Chlorophyllous areas — commonly olive grey (near 5 Y 3/1) (5 Y 4/1) (10 Y 3/1) (near 10 Y 4/1), greyish olive (5 Y 3/2) (5 Y 4/2) (7.5 Y 3/2) (7.5 Y 4/2) (10 Y 3/2) (10 Y 4/2), dark greyish olive (near 5 Y 2/1) (near 10 Y 2/1), greyish olive green (2.5 GY 3/2) (2.5 GY 4/2) and/or dark greenish grey (5 GY 3/1). (d) Scurfy band areas — commonly light yellowish pink (near 2.5 YR 8/4) (near 5 YR 8/4), moderate yellowish pink (near 2.5 YR 8/4) (near 5 YR 8/4), pale orange yellow (7.5 YR 8/4) (10 YR 8/4), light orange yellow (near 7.5 YR 8/6) (near 10 YR 8/6), moderate orange yellow (near 7.5 YR 8/6), pale yellow (near 2.5 Y 8/4) and/or greyish yellow (near 2.5 Y 8/4) in achlorophyllous areas and yellowish grey (near 10 YR 7/1) (5 Y 7/1) (5 Y 8/1) (10 Y 7/1) (10 Y 8/1) and/or light greenish grey (near 5 GY 7/1) (near 5 Gy 8/1 in chlorophyllous areas. 2. Lower epidermal surface: Scurfy surface that obscures colors which are commonly moderate purplish pink (near 7.5 RP 7/6), deep pink (10 RP 6/8), dark pink (near 5 R 6/6), strong pink (10 RP 7/8) (2.5 R 7/8), moderate pink (near 10 RP 8/4) (near 10 RP 8/6) (2.5 R 7/6) (10 RP 7/4) (10 RP 7/6) (near 2.5 R 8/4) (near 5 R 7/6) (near 5 R 8/4), light pink (near 10 RP 8/4) (near 10 RP 8/6) (near 2.5 R 8/4) (near 5 R 8/4) and/or strong yellowish pink (5 R 7/8) in achlorophyllous areas and pale yellow green (near 2.5 GY 8/2) (5 GY 8/2) (7.5 GY 8/2) and/or greyish yellow green (near 2.5 GY 7/2) (5 GY 7/2) (5 GY 6/2) (7.5 GY 7/2) (7.5 GY 6/2) in chlorophyllous areas.

Inflorescence:

A. *Form.*—1. General: Small sessile clusters that appear both in the terminal and in the axil areas of the upper leaves.

B. *Flowers.*—1. General: Sessile, actinomorphic with both staminate and bisexual flowers that have a calyx tube with three connate sepals, a corolla having three petals, epiptalous stamens that are usually 6 in number, anthers that are versatile and linear, filaments that are relatively short and cylindrical, the bisexual flowers having a compound pistil with three carpels, stigma limbs that are three in number, and an inferior ovary containing relatively few ovules. 2. Texture: Glabrous and fleshy 3. Shape: Elongated, triangular in transverse section in area of calyx tube and with divided petal lobing. 4. Size and color: Comparable to specimens of *Cryptanthus fosterianus* variety.

The following is a general description of a specimen of the new plant variety that was grown from the propagation of a vegetative offshoot in a nursery at Winter Garden, Fla.

A. Age of plant: Fourteen weeks from initial propagation of 8 month offshoot.

B. Diameter of plant (at base): About 29 cm. between opposite leaf tips.

C. Stem:

1. *Length.*—5 cm.
2. *Diameter.*—About 7 cm. at base.

D. Leaves:

1. *Number.*—12.
2. *Length.*—13 cm. (avg.).
3. *Width (max.).*—26 cm.
4. *Thickness.*—About 4 mm. along the axis.
5. *Color.*—(a) Upper epidermal side — (1) Chlorophyllous area: Olive grey (10 Y 3/1), greyish olive (10 Y 3/2) (7.5 Y 3/2), and/or dark greyish olive (near 10 Y 2/1). (2) Achlorophyllous areas: Dark purplish pink 7.5 RP 6/8, deep purplish pink 7.5 RP 6/10), moderate purplish red (7.5 RP 5/10). (3) Scurfy bands: -A- Chlorophyllous area — yellowish grey (10 Y 7/1) (10 Y 8/1) and/or light greenish grey (near 5 GY 8/1). -B- Achlorophyllous area — light yellowish pink (near 5 YR 8/4), moderate yellowish pink (near 5 YR 8/4), pale orange yellow (7.5 YR 8/4), light orange yellow (near 7.5 YR 8/6) and/or orange yellow (near 7.5 YR 8/6). (b) Lower epidermal side — (1) Chlorophyllous area: Pale yellow green (7.5 GY 8/2) and/or greyish yellow green (7.5 GY 7/2). (2) Achlorophyllous area: Purplish pink (7.5 R 7/6), strong pink (10 RP 7/8) and/or moderate pink (10 RP 8/4).

E. Inflorescence: Lacking.

I claim:

1. The new and distinct plant variety of the Bromeliaceae family substantially as shown and described herein.

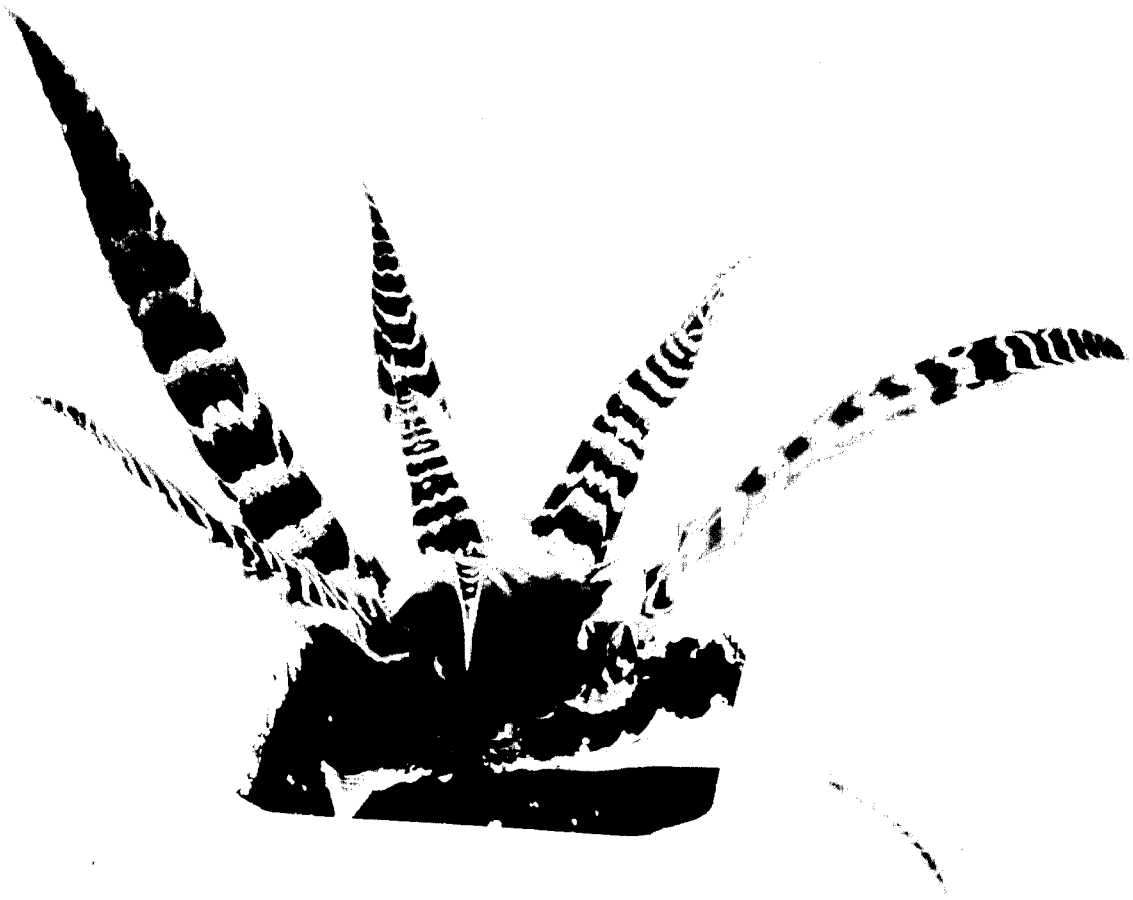

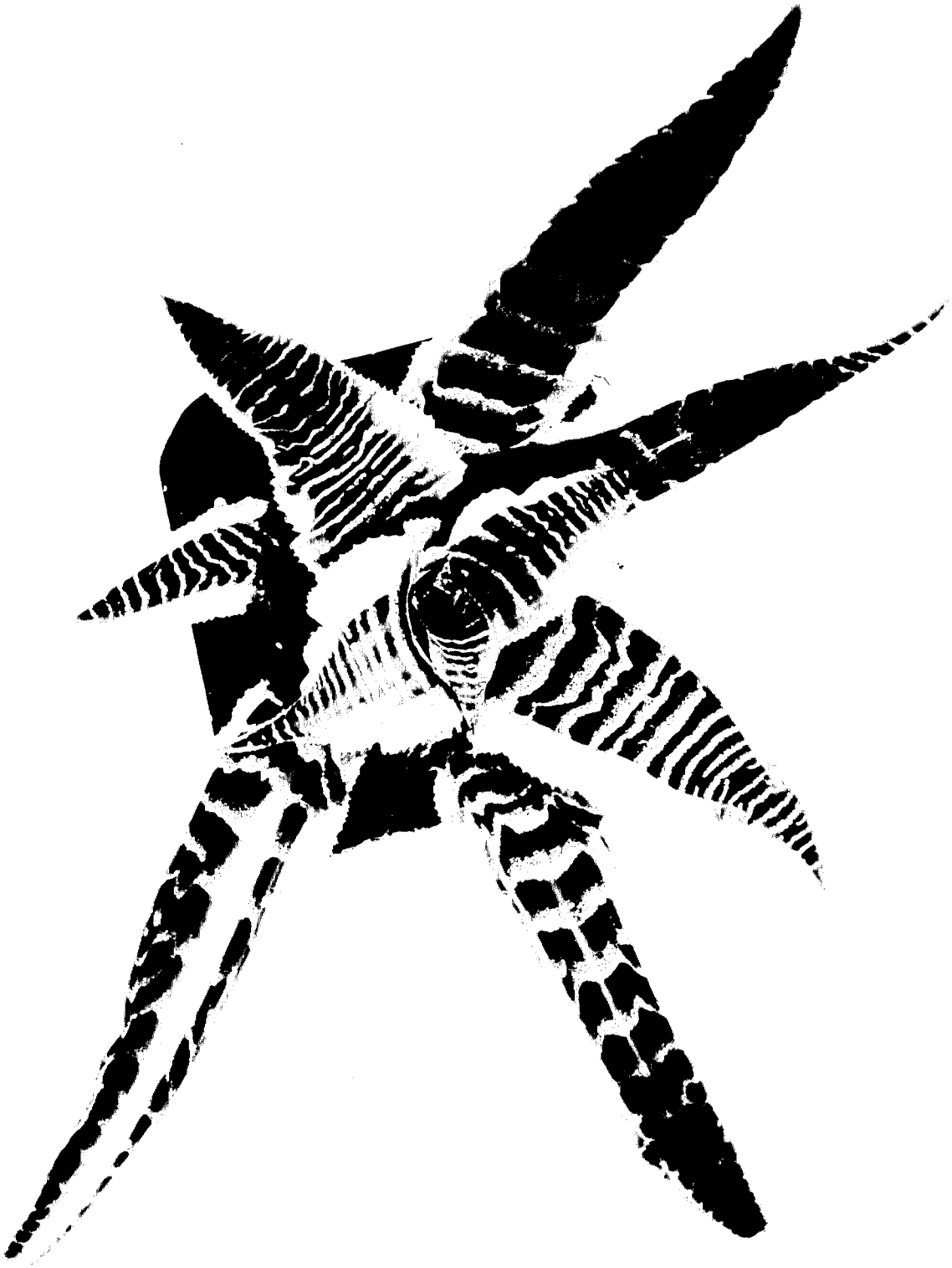

* * * * *